United States Patent
Datta et al.

(10) Patent No.: US 12,350,084 B2
(45) Date of Patent: Jul. 8, 2025

(54) SYSTEM AND METHOD FOR LiDAR GUIDED AUTO GATING IN A CT IMAGING SYSTEM

(71) Applicant: GE Precision Healthcare LLC, Wauwatosa, WI (US)

(72) Inventors: Arka Datta, Pewaukee, WI (US); Brian E. Nett, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 284 days.

(21) Appl. No.: 18/192,933

(22) Filed: Mar. 30, 2023

(65) Prior Publication Data
US 2024/0324977 A1    Oct. 3, 2024

(51) Int. Cl.
A61B 6/00 (2024.01)
A61B 6/03 (2006.01)
A61B 6/46 (2024.01)

(52) U.S. Cl.
CPC .............. *A61B 6/488* (2013.01); *A61B 6/032* (2013.01); *A61B 6/4435* (2013.01); *A61B 6/461* (2013.01)

(58) Field of Classification Search
CPC ....... A61B 6/488; A61B 6/032; A61B 6/4435; A61B 6/461; A61B 6/586; A61B 6/5264; A61B 6/545; A61B 6/547; A61B 6/035; A61B 6/0407; A61B 6/544; A61B 6/589
See application file for complete search history.

(56) References Cited

U.S. PATENT DOCUMENTS

| | | | |
|---|---|---|---|
| 7,632,015 B2 | 12/2009 | Stayman | |
| 8,417,315 B2 | 4/2013 | Mostafavi | |
| 8,939,920 B2 | 1/2015 | Maad | |
| 10,154,823 B2 | 12/2018 | Von Berg | |
| 10,376,217 B2 | 8/2019 | Schmidt | |
| 10,712,446 B1 | 7/2020 | Bills | |
| 10,737,118 B2 | 8/2020 | Mostafavi | |
| 10,823,955 B2 | 11/2020 | Sutton | |
| 11,276,166 B2 | 3/2022 | Prasad | |
| 2010/0074497 A1 | 3/2010 | Mielenz | |
| 2018/0360396 A1* | 12/2018 | Weng | G01S 5/30 |
| 2019/0122073 A1 | 4/2019 | Ozdemir | |
| 2021/0110594 A1 | 4/2021 | Teixeira | |
| 2021/0251516 A1 | 8/2021 | Santosh | |
| 2021/0353244 A1 | 11/2021 | Kiely | |
| 2021/0373160 A1 | 12/2021 | Kalscheur | |
| 2022/0015710 A1 | 1/2022 | Lewis | |

OTHER PUBLICATIONS

Li et al., "Augmented Reality-Guided Positioning System for Radiotherapy Patients," Journal of Applied Clinical Medical Physics, 2022, pp. 1-11, Wiley Periodicals, 11 pages.

* cited by examiner

*Primary Examiner* — Courtney D Thomas

(57) ABSTRACT

An imaging system and method for using the imaging system are described. In one example, a method of creating representative position information of a patient during a medical imaging scan is provided. The method includes, prior to performing a medical imaging scan, performing initial LiDAR data acquisition to obtain baseline LiDAR data, performing segmentation of the baseline LiDAR data, wherein the baseline LiDAR data includes a three-dimensional (3D) point cloud model, performing continuous LiDAR data acquisition to obtain continuous LiDAR data, which includes a real-time 3D point cloud model, and comparing the baseline LiDAR data with the continuous LiDAR data to detect motion of a patient.

18 Claims, 16 Drawing Sheets

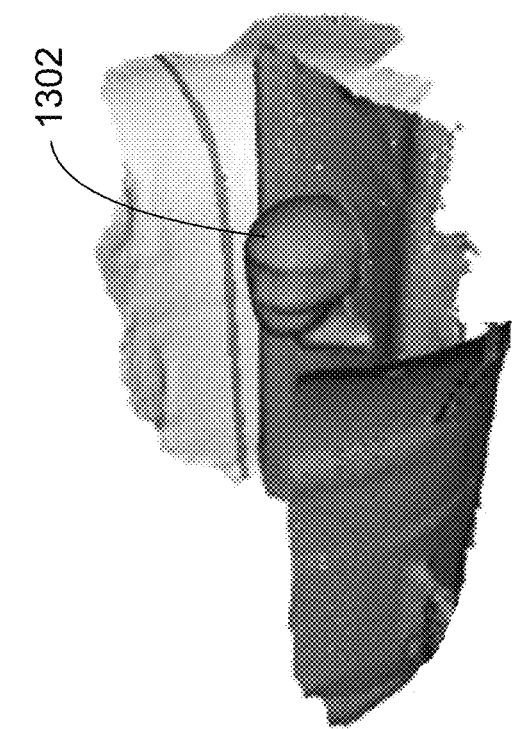
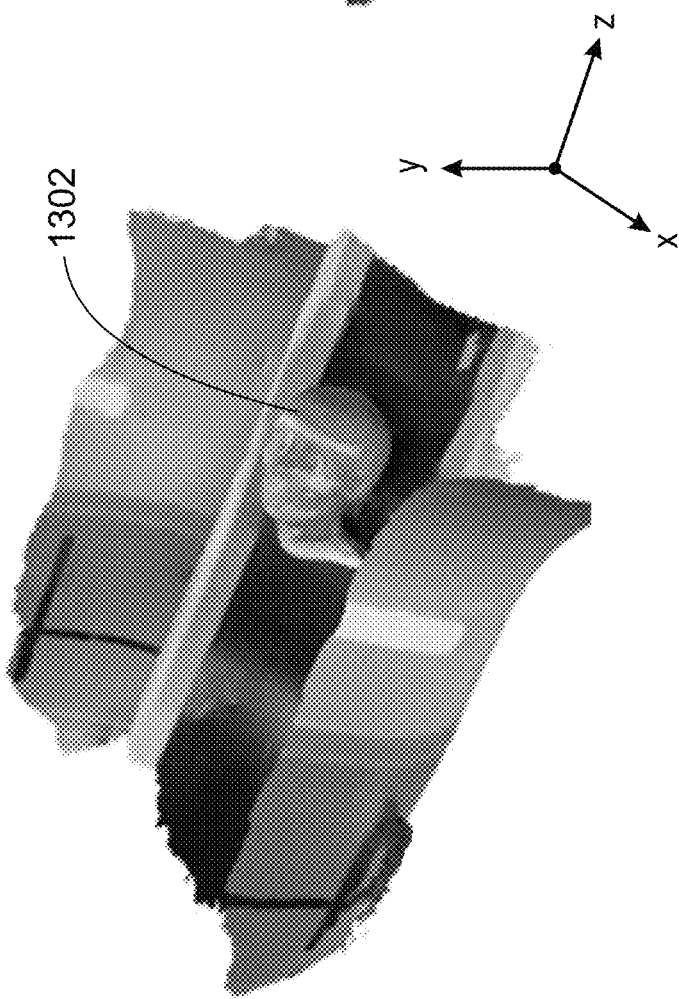
FIG. 13A
FIG. 13B

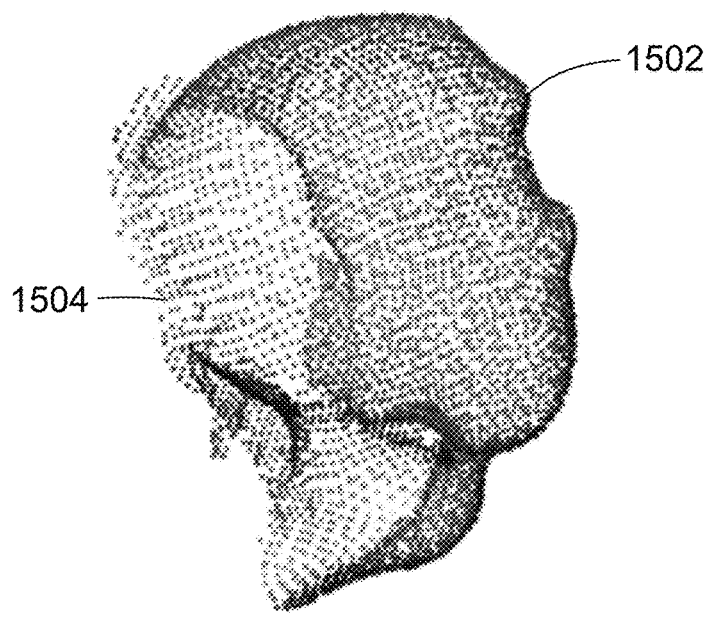
FIG. 15
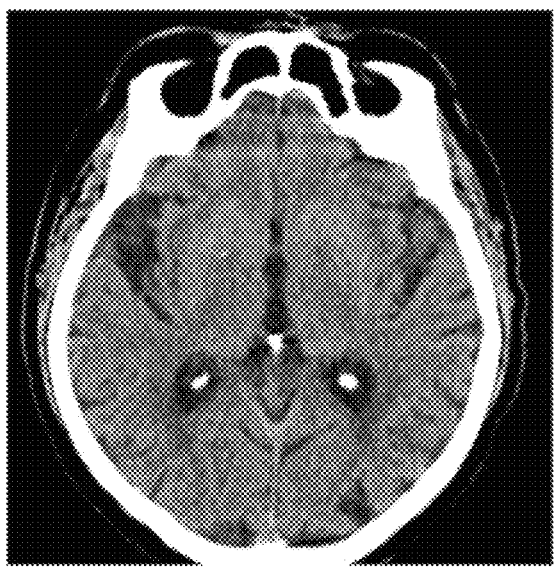 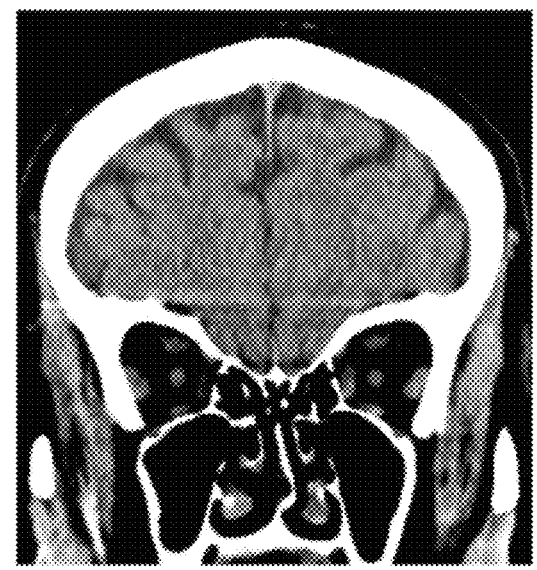
FIG. 16A  FIG. 16B

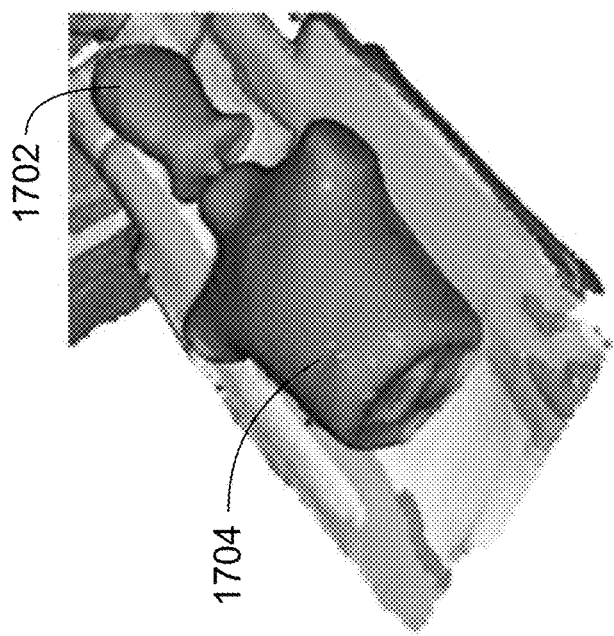
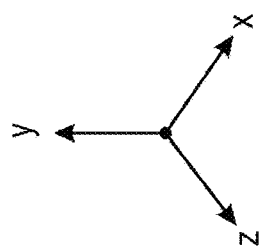
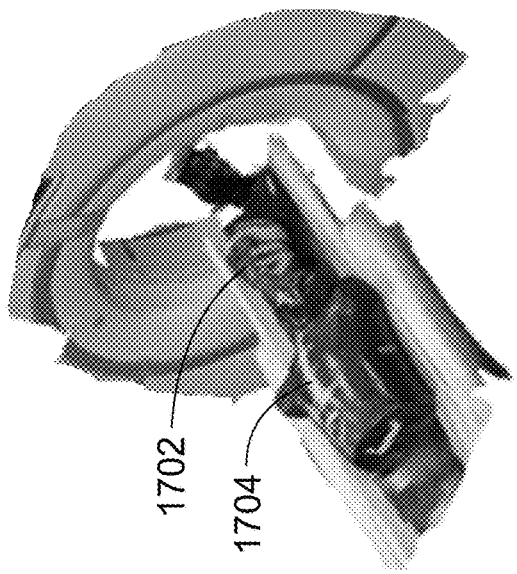
FIG. 17B
FIG. 17A

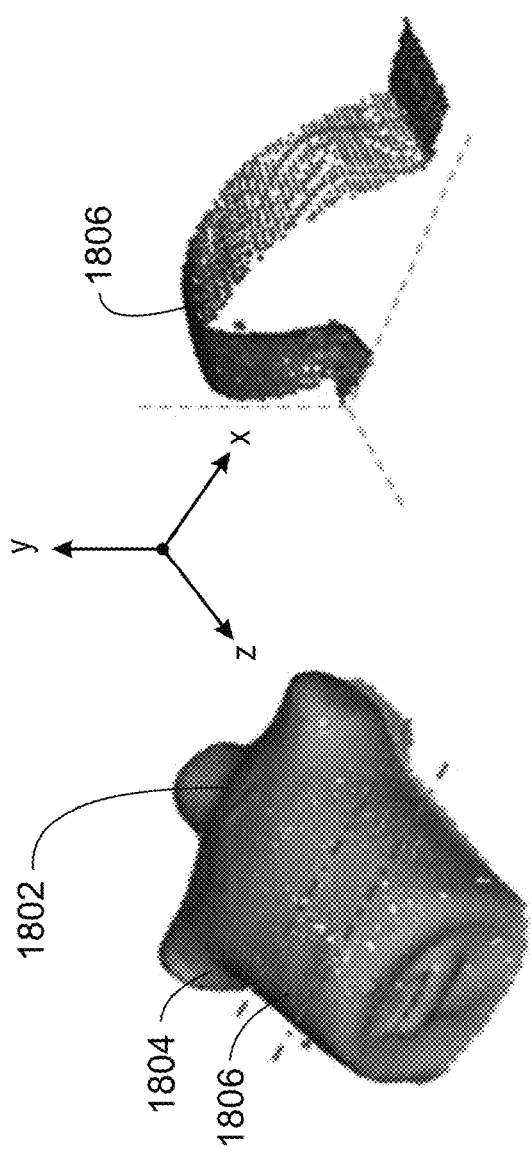

SYSTEM AND METHOD FOR LiDAR GUIDED AUTO GATING IN A CT IMAGING SYSTEM

BACKGROUND

The subject matter disclosed herein relates to medical imaging systems and, more particularly, to incorporation of laser imaging, detection and ranging (LiDAR) based techniques within a computed tomography (CT) imaging system.

In CT, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT imaging systems a detector array, including a series of detector elements or sensors, produces similar signals through various positions as a gantry is rotated around a patient, allowing volumetric reconstructions to be obtained.

An accurate three-dimensional (3D) measurement of a patient before or during a CT can significantly improve subsequent workflow (e.g., patient positioning, automated landmarking, etc.). Currently, regular-two dimensional (2D) images obtained with a regular camera cannot produce 3D information. A 3D scout acquisition (e.g., a CT imaging scan acquired utilizing a radiation dose lower than typically utilized during a diagnostic CT imaging scan) may address this issue but with the expense of an additional dose. For example, using the 3D measurement and of a patient and position information obtained from the measurement can help determine movement of the patient.

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below. This summary introduces concepts that are described in more detail in the detailed description. It should not be used to identify essential features of the claimed subject matter, nor to limit the scope of the claimed subject matter.

In one aspect, a method of creating representative position information of a patient during a medical imaging scan is provided. The method includes, prior to performing a medical imaging scan, performing initial LiDAR data acquisition to obtain baseline LiDAR data, performing segmentation of the baseline LiDAR data to create point cloud reference information, wherein the reference information includes a three-dimensional (3D) point cloud model, performing continuous LiDAR data acquisition to obtain real-time point cloud data, and comparing the real-time point cloud data with the point cloud reference information to detect motion of a patient.

In another aspect, a medical imaging system is provided. The medical imaging system includes a gantry having a bore, rotatable about an axis of rotation, an X-ray source mounted on the gantry and configured to emit an X-ray beam, an X-ray controller to operate the X-ray source, a detector configured to detect the X-ray beam emitted by the radiation source, and a laser imaging, detection and ranging (LiDAR) scanning system physically coupled to the CT imaging system. The LiDAR scanning system includes a LiDAR instrument mounted on the gantry, a LiDAR controller to control operation of the LiDAR instrument, and a LiDAR data processing unit to obtain pre-scan data from the LiDAR instrument, wherein the LiDAR data processing unit generates a baseline 3D point cloud of the subject using the pre-scan data, and wherein the LiDAR processing unit obtains real-time data during a scan to generate additional 3D point clouds, wherein the additional 3D point clouds are compared to the baseline 3D point cloud to detect movement of a subject. The imaging system also includes a processor to, when the LiDAR data processing unit detects movement of the subject, abort a scan.

BRIEF DESCRIPTION OF THE DRAWINGS

These and other features, aspects, and advantages of the present disclosed subject matter will become better understood when the following detailed description is read with reference to the accompanying drawings in which like characters represent like parts throughout the drawings, wherein:

FIG. 13A depicts LiDAR data of an example phantom head.

FIG. 13B depicts segmentation of the example phantom head of FIG. 13A.

FIG. 15 depicts an example 3D segmented LiDAR point cloud created using data obtained using the LiDAR scanning system.

FIGS. 16A and 16B depict examples of motion artifacts in images obtained during a CT scan.

FIGS. 17A and 17B depict example detailed representations of LiDAR data and segmented LiDAR data.

FIGS. 18A-18C depict example segmented LiDAR point clouds of regions isolated from LiDAR scanning data.

DETAILED DESCRIPTION

Figure 1:
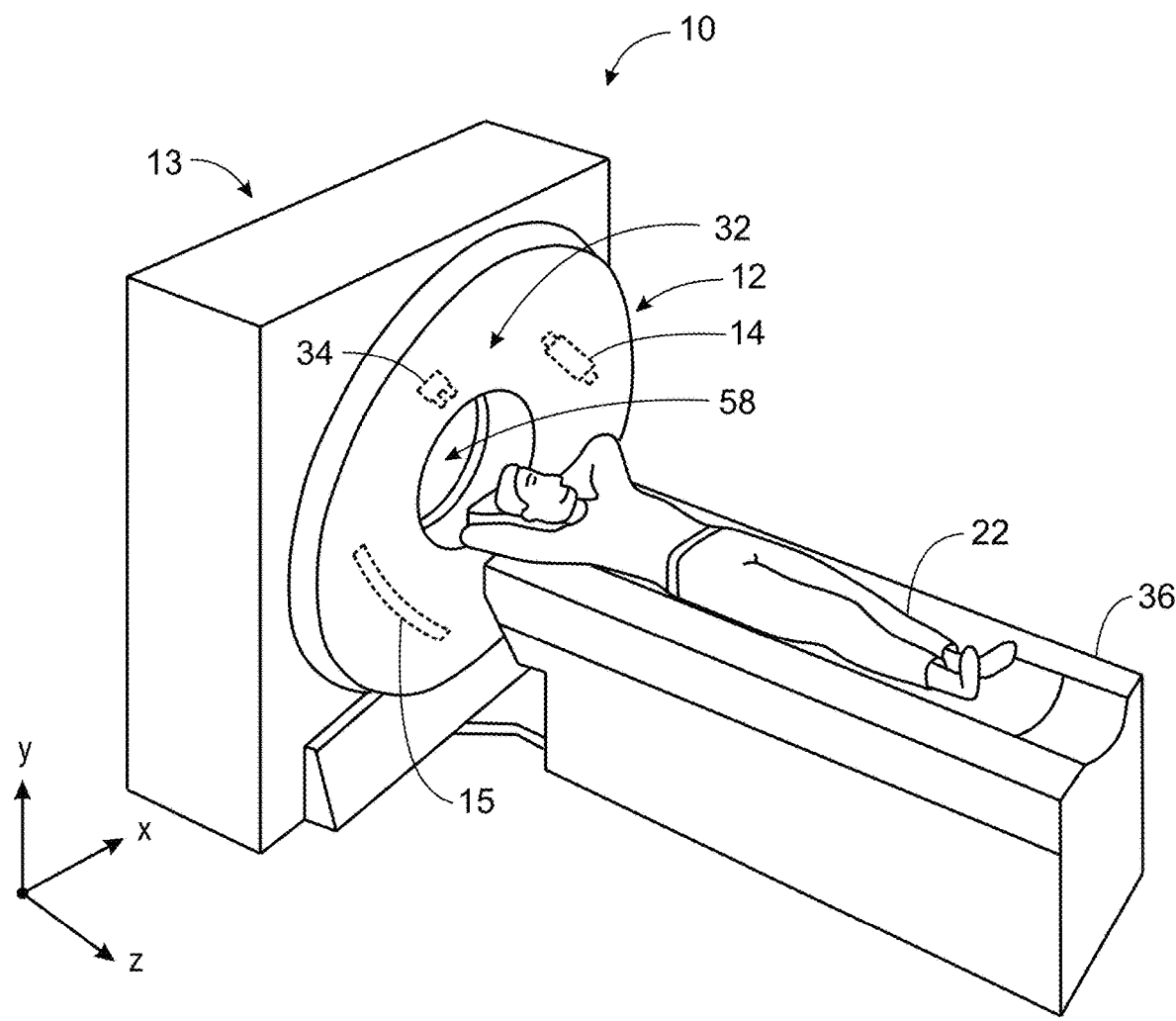
FIG. 1 is a pictorial representation of a CT imaging system, in accordance with aspects of the present disclosure.

Embodiments of the present disclosure will now be described, by way of example, with reference to the Figures. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context to provide accurate three-dimensional (3D) information of a target to improving workflow processes and post processing steps.

The present disclosure provides systems and methods for incorporating LiDAR based techniques with a CT imaging system to aid various workflows more efficiently. A LiDAR system is a remote sensing method to measure target objects a variable distance from a source. With the advancement of LiDAR technique, it can now produce 3D rendering of a subject with high spatial resolution (e.g., sub millimeter (mm) accuracy). The disclosed techniques do not need any X-ray radiation to image the target or patient and only require time of flight information of reflected pulsed light (e.g., laser) to calculate and reproduce 3D information (e.g., depth dependent information) of the patient. The time of flight information may calculate depth, which may be used to create a 3D model of a patient undergoing a CT scan and to detect motion of the patient undergoing the CT scan. Multiple views are utilized to cover an entire target area to reproduce high fidelity 3D information. In certain embodiments, light images may be acquired by moving the data acquisition system (i.e., LiDAR scanning system having one or more LiDAR scanners or instruments) around the target (e.g., around the gantry). In some embodiments, the LiDAR scanners or system is integrated within the CT imaging system. In this embodiment, the data acquisition system may be integrated outside the scan window (and, thus, physically coupled to the CT imaging system) and rotated to capture multiple views. In certain embodiments, multiple LiDAR scanners or instruments may be placed at different angular positions around the patient to capture the entire region of interest. In certain embodiments, a LiDAR scanning system (e.g., having multiple LiDAR scanners or instruments) may be mounted externally relative to the gantry (e.g., on the scanner housing or the CT table) but still be physically coupled to the CT imaging system. The external LiDAR scanning system may be place in position as required by a guided rail system. The LiDAR-based data may be acquired prior to, during, and subsequent to a CT scan of the target or patient. The LiDAR-based data can be processed and utilized for subsequent (i.e., after the LiDAR scan) workflow processes (e.g., accurate light scout measurement, proper patient positioning and automated landmarking, etc.) and post-processing steps (e.g., image reconstruction). The disclosed embodiments provide a holistic framework for including a LiDAR scanning system in a CT imaging system to improve overall efficiency and robustness of the workflow processes and post-processing steps.

The present disclosure also provides a method of detecting a position of an object positioned for an imaging scan using a LiDAR scanning system. The example LiDAR scanning system provides data related to the position of the object, specifically 3D point cloud information of the object. The position information data can be compared to an imaging protocol to determine if the position of the object corresponds to the protocol (i.e., the right portion of the object is positioned to be imaged). Additionally, the position information can be used during the imaging scan to detect movement of the object or subject. If movement is detected, the imaging system can account for the movement by aborting the scan or by removing the view from the imaging scan that include movement. Thus, the image quality can be improved by accounting for the movement of the subject.

Figure 2:
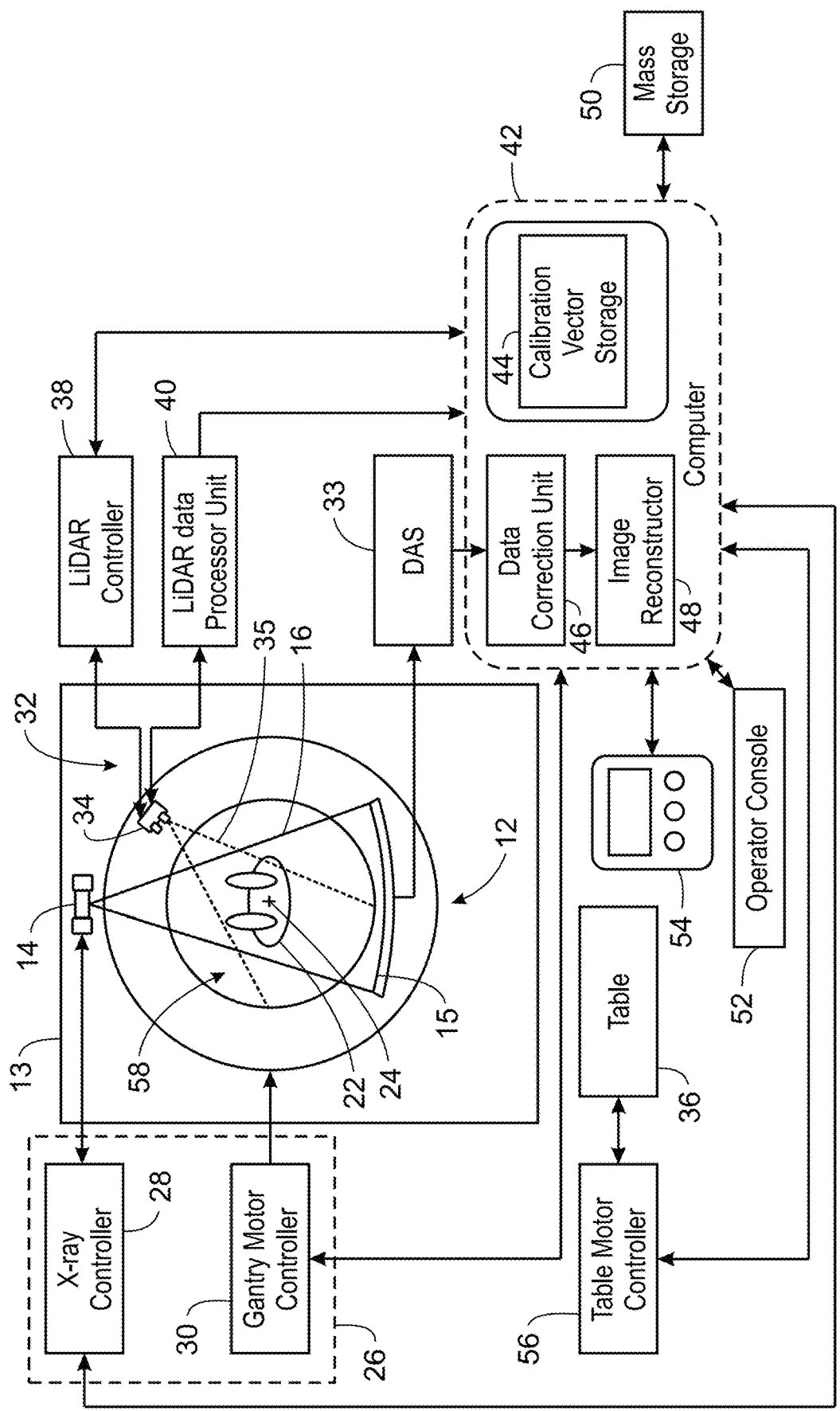
FIG. 2 is a block diagram of the CT imaging system in FIG. 1, in accordance with aspects of the present disclosure.

With the preceding in mind and referring to FIGS. 1 and 2, a CT imaging system 10 is shown, by way of example. The CT imaging system 10 includes a gantry 12 enclosed within a housing 13 (e.g., gantry housing). The gantry 12 has a rotating component and a stationary component. The gantry 12 has an X-ray source 14 that projects a beam of X-rays 16 toward an X-ray detector assembly or X-ray detector array 15 (e.g., having a plurality of detector modules) on the opposite side of the gantry 12. The X-ray source 14 and the X-ray detector assembly 15 are disposed on the rotating portion of the gantry 12. The X-ray detector assembly 15 is coupled to a data acquisition system (DAS) 33. The plurality of detector modules of the X-ray detector assembly 15 detect the projected X-rays that pass through a patient or subject 22, and DAS 33 converts the data to digital signals for subsequent processing. Each detector module of the X-ray detector assembly 15 in a conventional system produces an analog electrical signal that represents the intensity of an incident X-ray beam and hence the attenuated X-ray beam as it passes through the patient 22. During a scan to acquire X-ray projection data, gantry 12 and the components mounted thereon rotate about a center of rotation 24 (e.g., isocenter) so as to collect attenuation data from a multitude of view angles relative to the imaged volume.

Rotation of gantry 12 and the operation of X-ray source 14 are governed by a control mechanism 26 of CT imaging system 10. Control mechanism 26 includes an X-ray controller 28 that provides power and timing signals to the X-ray source 14 and a gantry motor controller 30 that controls the rotational speed and position of gantry 12.

The imaging system 10 also includes a laser imaging, detection and ranging (LiDAR) scanning system 32 physically coupled to the imaging system 10. The LiDAR scanning system 32 includes one or more LiDAR scanners or instruments 34. As depicted, the LiDAR scanning system 32 has one LiDAR scanner 34. The one or more LiDAR scanners 34 are utilized to acquire depth dependent information (LiDAR data or light images) of the patient 22 with high spatial fidelity. The depth dependent information is utilized in subsequent workflow processes for a CT scan. The one or more LiDAR scanners 34 emit pulsed light 35 (e.g., laser) at the patient 22 and detect the reflected pulsed light from the patient 22. The LiDAR scanning system 32 is configured to acquire the LiDAR data from multiple different views (e.g., at different angular positions relative to the axis of rotation 24).

In certain embodiments, as depicted in FIGS. 1 and 2, the LiDAR scanner 34 is coupled to the gantry 12. In particular, the LiDAR scanner 34 is disposed within the gantry housing 13 outside a scan window. The LiDAR scanner 34 is rotated around the patient 22 to acquire the LiDAR data at the different angular positions. In certain embodiments, multiple LiDAR scanners 34 may be coupled to the gantry 12 and rotated to acquire the LiDAR data at the different angular positions.

In certain embodiments, multiple LiDAR scanners 34 may be coupled to the gantry 12 in fixed positions but disposed at different angular positions (e.g., relative to axis of rotation 24). The LiDAR scanners 34 in fixed positions may acquire the LiDAR data at the same time while remaining stationary.

In certain embodiments, the LiDAR scanning system 32 may be external to the gantry 12 but still physically coupled to the imaging system 10. For example, multiple LiDAR scanners 34 may be coupled to a LiDAR panel (e.g., at different angular positions relative to the axis of rotation 24) that is coupled to a guide rail system. The guide rail system may be coupled to the gantry housing 13 or a table 36 of the system 10. The guide rail system may be configured to move the LiDAR panel toward and away from the gantry 12. In certain embodiments, the guide rail system may also be configured to rotate the LiDAR panel about the axis of rotation 24.

The LiDAR scanning system 32 includes a LiDAR controller 38 configured to provide timing and control signals to the one or more LiDAR scanners 34 for acquiring the LiDAR data at the different angular positions. The LiDAR data may be acquired prior to, during, and/or subsequent to a CT scan of the patient 22. The LiDAR scanning system 32 also includes a LiDAR data processing unit 40 that receives or obtains the LiDAR data from the one or more LiDAR scanners 34. The integrated LiDAR system and/or the LiDAR data processing unit 40 utilizes time of flight information of the reflected pulsed light and processes the LiDAR data (e.g., acquired at the different views) to generate an accurate 3D measurement of the patient 22. The 3D measurement of the patient 22 has a high spatial resolution (e.g., sub mm accuracy). As noted above, the 3D measurement may be utilized in subsequent workflow processes of a CT scan. For example, the 3D measurement may be utilized as an accurate light scout measurement (e.g., for modifying scan acquisition parameters). The 3D measurement may also be utilized for proper patient positioning (e.g., for modifying or optimizing patient position parameters) and automated landmarking. The 3D measurement may further be utilized for post-processing such as in an image reconstruction algorithm of the CT scan data (e.g., modifying reconstruction parameters).

The 3D measurement information from the LiDAR scanning system 32 (e.g., from the LiDAR data processing unit 40) and the scan data from the DAS 33 is input to a computer 42. The computer 42 includes a calibration vector storage 44 (e.g., for storing calibration parameters and calibration protocols for acquiring the CT scan data). The 3D measurement information obtained from the LiDAR scanning system 32 may be utilized in determining the calibration parameters utilized. The computer 42 also includes a data correction unit 46 for processing or correcting the CT scan data from the DAS 33. The computer 42 further includes an image reconstructor 48. The image reconstructor 48 receives sampled and digitized X-ray data from DAS 33 and performs high-speed reconstruction. The reconstructed image is applied as an input to the computer 42, which stores the image in a mass storage device 50. Computer 42 also receives commands and scanning parameters from an operator via console 52. An associated display 54 allows the operator to observe the reconstructed image as well as the 3D measurement data and other data from the computer 42. The operator supplied commands and parameters are used by computer 42 to provide control signals and information to the DAS 33, X-ray controller 28, gantry motor controller 30, and the LiDAR controller 38. In addition, computer 42 operates a table motor controller 56, which controls a motorized table 36 to position the patient 22 relative to the gantry 12. Particularly, table 36 moves portions of the patient 22 through a gantry opening or bore 58.

The computer 42 and the LiDAR processor unit 40 include may each include processing circuitry. The processing circuitry may be one or more general or application-specific microprocessors. The processing circuitry may be configured to execute instructions stored in a memory to perform various actions. For example, the processing circuitry may be utilized for receiving or obtaining LiDAR data acquired with the LiDAR scanning system 32. In addition, the processing circuitry may also generate a 3D measurement of the patient 22. Further, the processing circuitry may utilize the 3D measurement in a subsequent workflow process for a CT scan of the patient with the CT imaging system 32.

Figure 3:
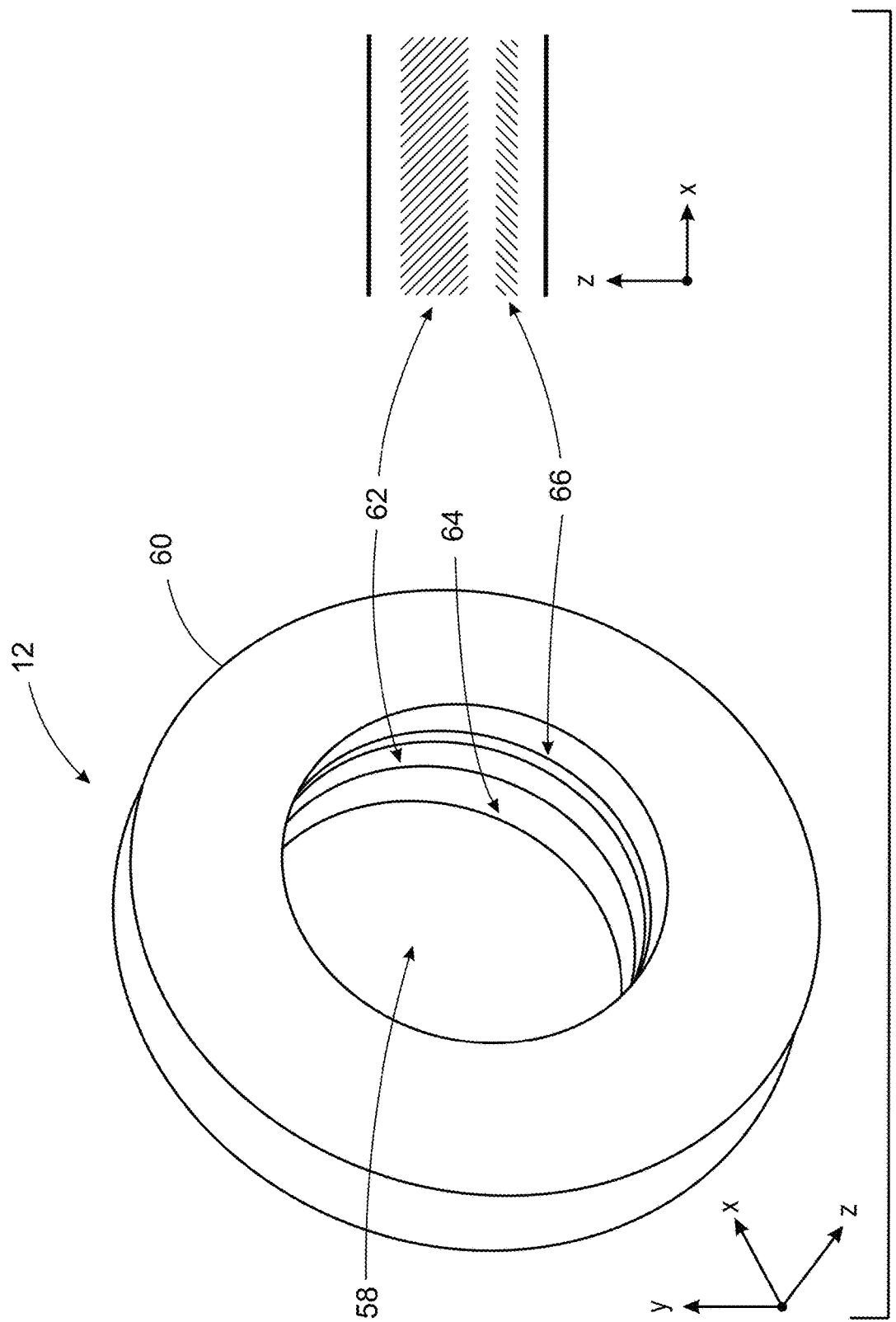
FIG. 3 is a schematic diagram of a LiDAR window placement within a gantry of a CT imaging system, in accordance with aspects of the present disclosure.

FIG. 3 is a schematic diagram of LiDAR window placement within the gantry 12 of a CT imaging system. The gantry 12 includes a gantry cover 60 configured to be located on a front portion of the gantry housing adjacent the CT table, and located on a rear portion of the gantry housing. The CT imaging system includes an annular scan window 62 disposed within an interior wall 64 of the gantry 12 formed within the opening or the bore 58 of the gantry 12. The scan window 62 is made of an X-ray transparent material that enables X-rays emitted from an X-ray source to pass through an object or subject being imaged for detection by a detector.

The scan window 62 is constructed so as to be fitted between components of the housing of the gantry 12 (e.g., front and back covers) to fill a gap. During an imaging session, a subject or patient is moved within the bore 58. The scan window 62 self-supports and acts as a safety barrier to keep the subject or patient from contacting rotating components within the gantry 12.

As depicted, an annular LiDAR panel or window 66 is also disposed within the interior wall 64 of the gantry 12 formed within the bore 58 of the gantry 12. The LiDAR panel 66 is made of a material transparent to the pulsed light (e.g., laser) emitted by one or more LiDAR scanners disposed within gantry 12 toward the object or subject and reflected back to the one or more LiDAR scanners. The LiDAR panel 66 is disposed between scan window 62 and the gantry cover 60 in the Z-direction. In particular, the LiDAR panel 66 is disposed between the scan window 62 and a front of the gantry 12 adjacent the CT table. During an imaging session, a subject or patient is moved within the bore 58. The LiDAR panel 66 also self-supports and acts as a safety barrier to keep the subject or patient from contacting components (e.g., sometimes rotating components) within the gantry 12. The one or more LiDAR scanners may be located within the gantry 12 behind the LiDAR panel 66. In certain embodiments, the one or more LiDAR scanners 34 are stationary during acquisition of LiDAR data. In certain embodiments, the one or more LiDAR scanners rotate during acquisition of LiDAR data. The LiDAR panel 66 is located outside the region of the subject or object being scanned by the CT imaging system.

Figure 4:
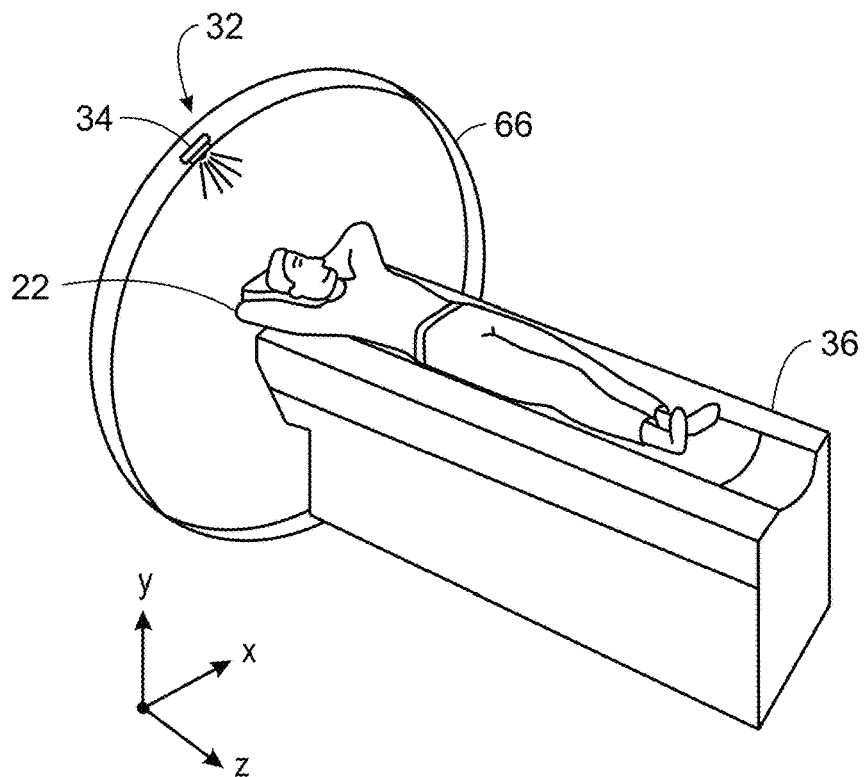
FIG. 4 is a perspective view of a schematic diagram of a LiDAR scanning system relative to a patient on a CT table, in accordance with aspects of the present disclosure.

FIG. 4 is a perspective view of a schematic diagram of the LiDAR scanning system 32 relative to the patient on the CT table 36. With the exception of the LiDAR scanning system 32, the components of the gantry are not shown for simplification. One or more LiDAR scanners 34 may be coupled to the LiDAR panel or window 66. As depicted, a single LiDAR scanner 34 is coupled to the LiDAR panel 66. In certain embodiments, multiple LiDAR scanners 34 may be disposed at different circumferential positions (e.g., different angular positions relative to the axis of rotation 24 in FIG. 2) along the LiDAR panel 66. The LiDAR panel 66 is disposed within the inner wall of the gantry formed within the bore of the gantry. The LiDAR scanners 34 are arranged in a concentric manner with the LiDAR panel 66 (e.g., relative to the axis of rotation 24) with the LiDAR panel 66 being located radially closer (in the Y-direction) than the LiDAR scanners 34 to the axis of rotation 24. In certain embodiments, the LiDAR panel 66 and associated LIDAR scanners 34 remain in a fixed position, while LiDAR scanners 34 acquire the LiDAR data at different angular positions. In certain embodiments, the LiDAR panel 66 and one or more associated LiDAR scanners 34 rotate to acquire the LiDAR data.

Figure 5A:
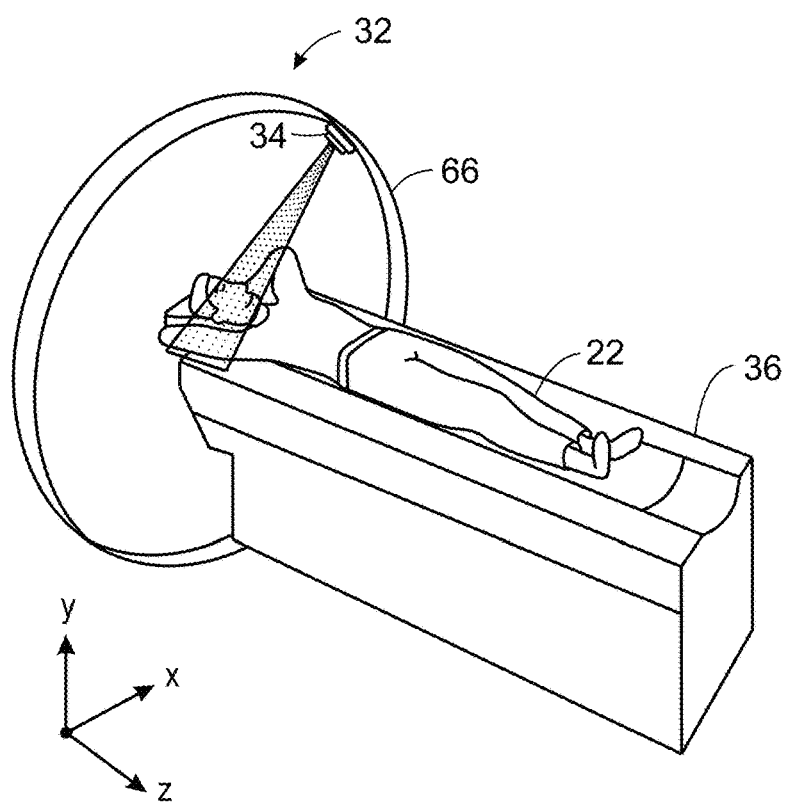
FIGS. 5A-5C depict a single LiDAR scanner obtaining data at different angular positions, in accordance with aspects of the present disclosure.
Figure 5B:
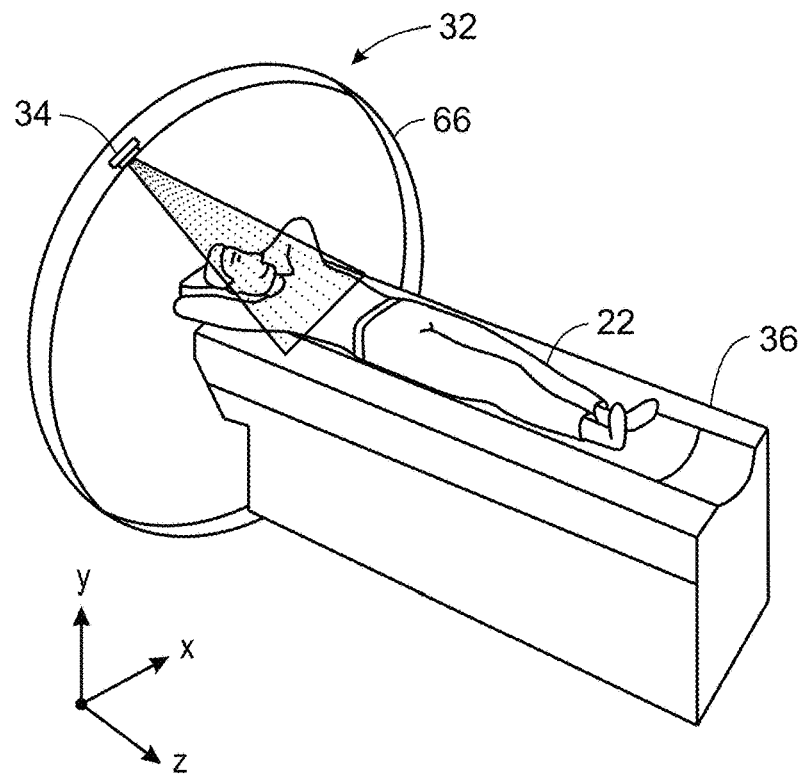
Figure 5C:
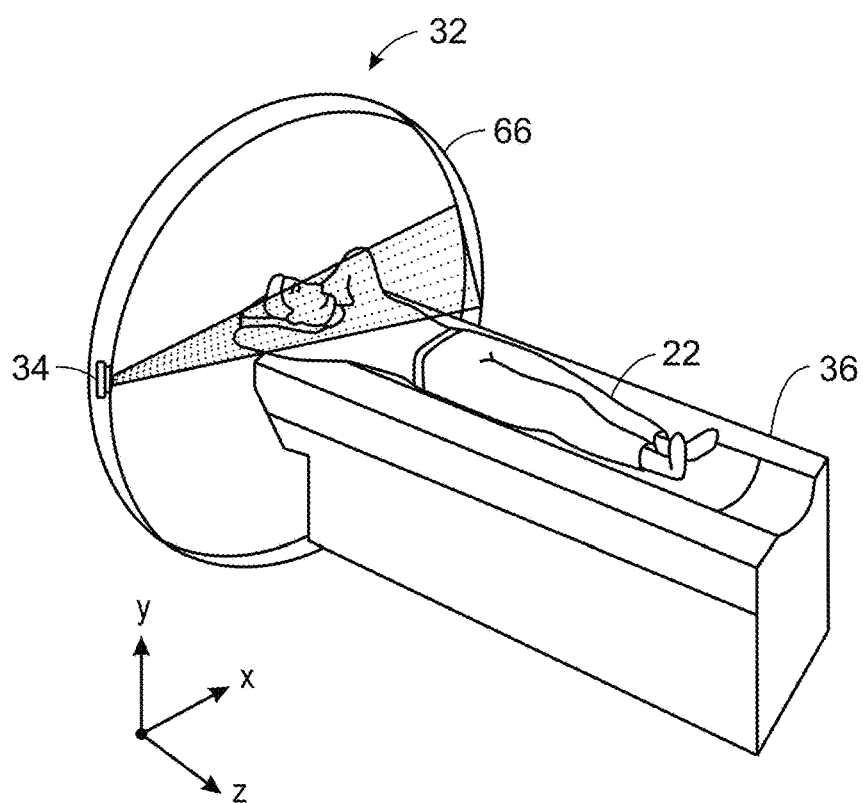
Figure 6:
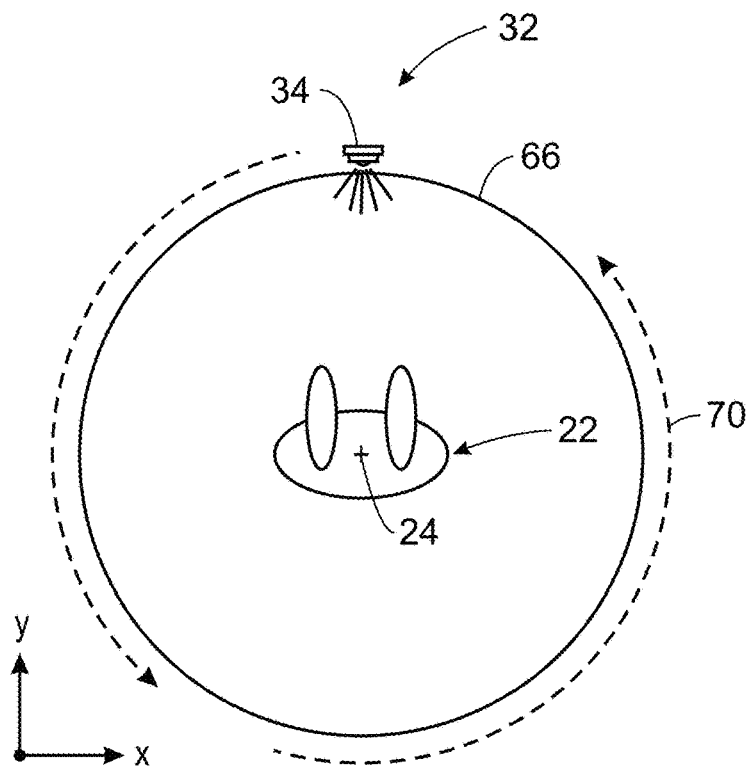
FIG. 6 is a pictorial representation of a single LiDAR scanner rotating 360 degrees around a patient for data acquisition, in accordance with aspects of the present disclosure.

FIGS. 5A-5C depict a single LiDAR scanner 34 obtaining data at different angular positions. With the exception of the LiDAR scanning system 32, the components of the gantry are not shown for simplification. As depicted in FIGS. 5A-5C, the single LiDAR scanner 34 is coupled to the LiDAR panel 66. The LiDAR scanner 34 rotates (e.g., about the axis of rotation 24 in FIG. 2) to acquire the LiDAR data. In particular, the LiDAR scanner 34 (and LiDAR panel 66) rotates to different angular positions to acquire different views of LiDAR data. The data acquired at the different angular positions can then be combined later to generate the 3D measurement of the patient 22. It should be noted although the patient 22 is depicted outside an area of the gantry where the LiDAR panel 66 is located, in certain embodiments, the patient 22 may be moved into the gantry via the table 36 so that the LiDAR panel 66 is disposed about a portion of the patient 22. As depicted in FIG. 6, the single LiDAR scanner 34 may rotate up to 360 degrees in a circumferential direction 70 (e.g., relative to the axis of rotation 24) around the target (i.e., the patient 22) to acquire the LiDAR data at the different angular positions.

Figure 7:
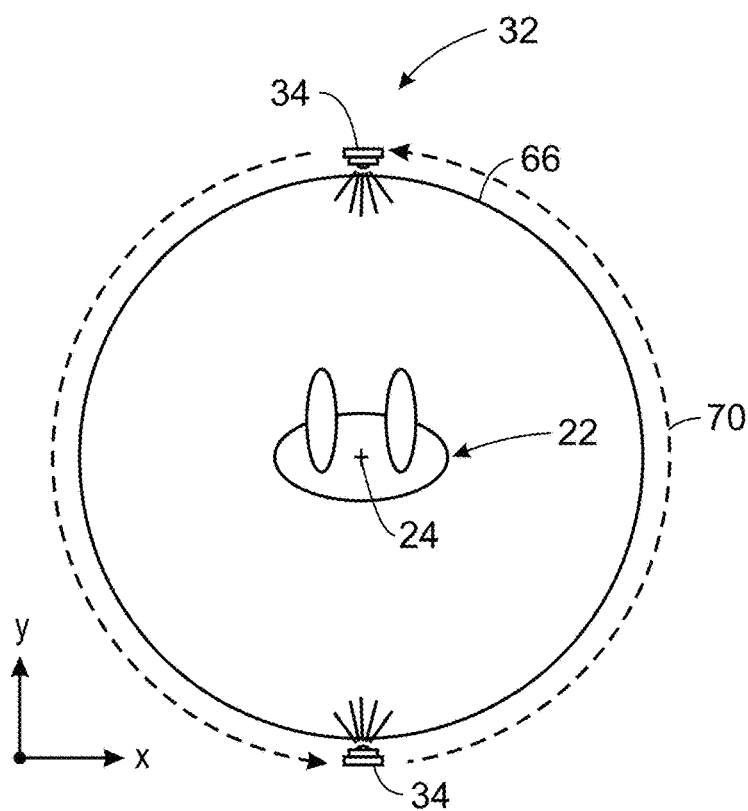
FIG. 7 is a pictorial representation of multiple LiDAR scanners rotating around a patient for data acquisition, in accordance with aspects of the present disclosure.

In certain embodiments, as depicted in FIG. 7, multiple LiDAR scanners 34 may be coupled to the LiDAR panel 66. As depicted, two LiDAR scanners 34 are coupled to the LiDAR panel 66. The number of LiDAR scanners 34 coupled to the LiDAR panel 66 may vary (e.g., 2, 3, 4, 5, 6, or other number of LiDAR scanners 34). The LiDAR scanners 34 are circumferentially 70 spaced apart from each other along the LiDAR panel 66. Each LiDAR scanner 34 (and the LiDAR panel 66) rotates about the axis of rotation 24. In certain embodiments, each LiDAR scanner 34 rotates only a portion of the 360 degrees around the patient 22 to acquire the LiDAR data. For example, as depicted in FIG. 7, each LiDAR scanner 34 may rotate only up to approximately 180 degrees circumferentially 70. Thus, together both the LiDAR scanners 34 may cover 360 degrees about the patient 22. In certain embodiments, with three LiDAR scanners 34 coupled to the LiDAR panel 66, each LiDAR scanner 34 may cover up to approximately 120 degrees circumferentially 70. In certain embodiments, with four LiDAR scanners 34 coupled to the LiDAR panel 66, each LiDAR scanner 34 may cover up to approximately 90 degrees circumferentially 70. Thus, no matter the number of LiDAR scanners 34 coupled to the LiDAR panel 66, each LiDAR scanner 34 may cover an equal portion of the 360 degrees about the patient 22. In certain embodiments, when multiple LiDAR scanners 34 are coupled to the LiDAR panel 66, one or more of the LiDAR scanners 34 cover a different angular range about the patient 22 relative to the other LiDAR scanners 34. For example, in the case of two LiDAR scanners 34, one LiDAR scanner 34 may cover 120 degrees and the other LiDAR scanner may cover 240 degrees. In certain embodiments, when multiple LiDAR scanners 34 are coupled to the LiDAR panel 66, each LiDAR scanner 34 may cover up to 360 degrees to provide redundancy in the acquired data. In certain embodiments, the LiDAR scanning system 32 may not cover 360 degrees about the patient 22 when certain angular positions are obstructed (e.g., by a bottom of the CT table).

Figure 8:
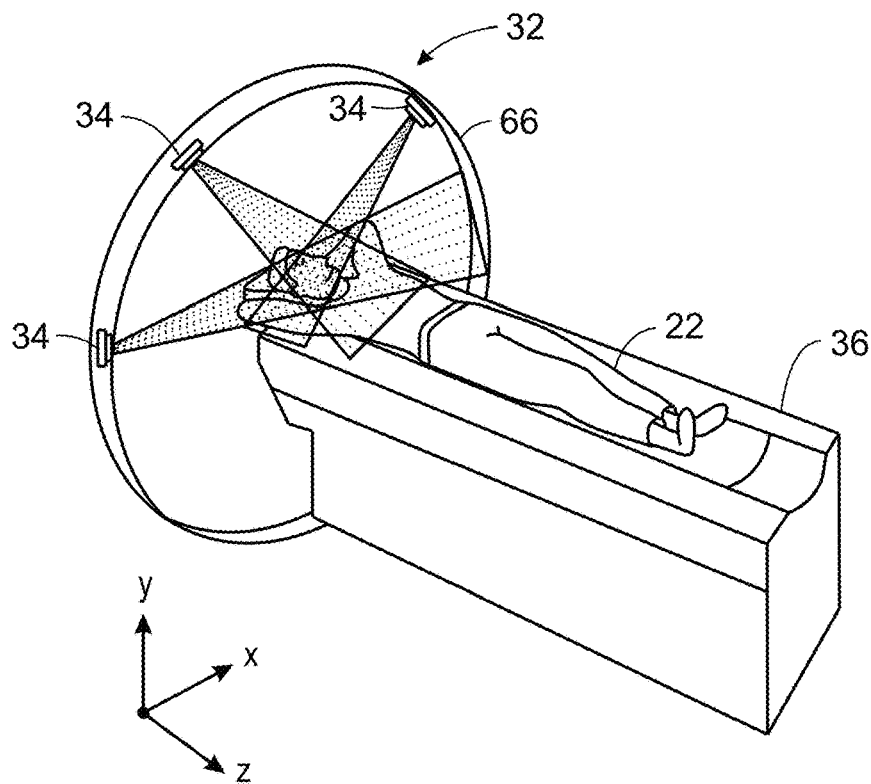
FIG. 8 is a perspective view of a schematic diagram of multiple LiDAR scanners obtaining data of a patient at different angular positions at the same time; in accordance with aspects of the present disclosure.
Figure 9:
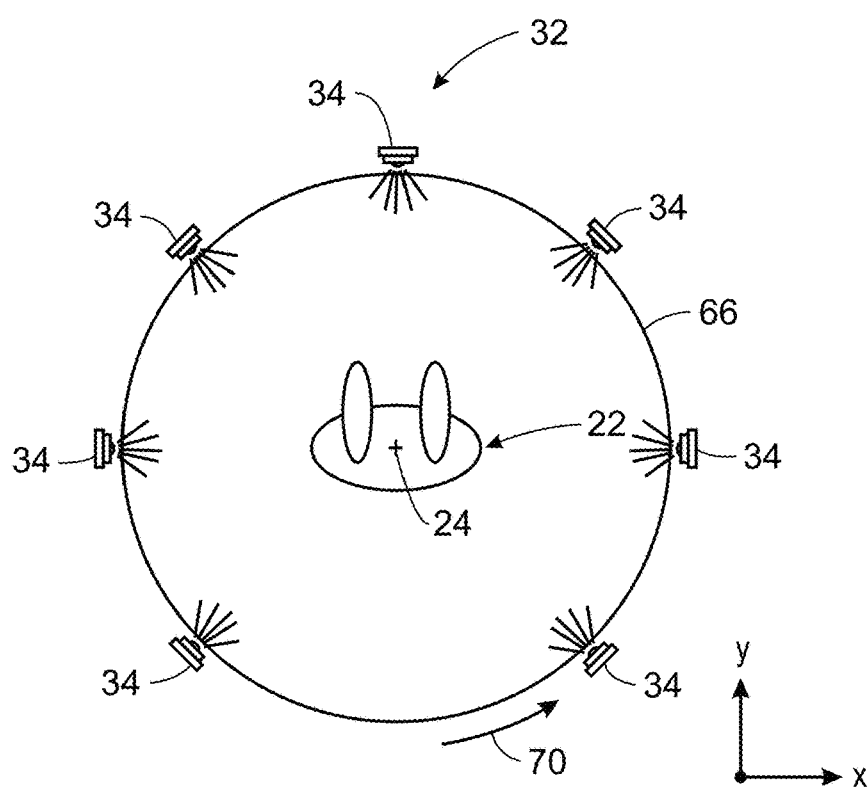
FIG. 9 is a pictorial representation of multiple LiDAR scanners placed 360 degrees around the patient for data acquisition, in accordance with aspects of the present disclosure.

FIGS. 8 and 9 illustrate utilizing multiple LiDAR scanners 34 to obtain data of the patient 22 at different angular positions at the same time. With the exception of the LiDAR scanning system 32, the components of the gantry are not shown for simplification. As depicted, the LiDAR scanning system 32 includes multiple LiDAR scanners 34 coupled to the LiDAR panel 66. The LiDAR scanners 34 are circumferentially 70 spaced apart (e.g., relative to the axis of rotation 24) from each other along the LiDAR panel 66. The LiDAR scanners 34 are disposed in fixed positions (e.g., different angular positions) along the LiDAR panel 66. Both the LiDAR scanners 34 and LiDAR panel 66 remain stationary during acquisition of the LiDAR data. In particular, LiDAR data is acquired by each of the LiDAR scanners 34 scanners at the same time, thus, providing LiDAR data at different views (i.e., different angular positions). The data acquired at the different angular positions can then be combined later to generate the 3D measurement of the patient 22.

Figure 10:
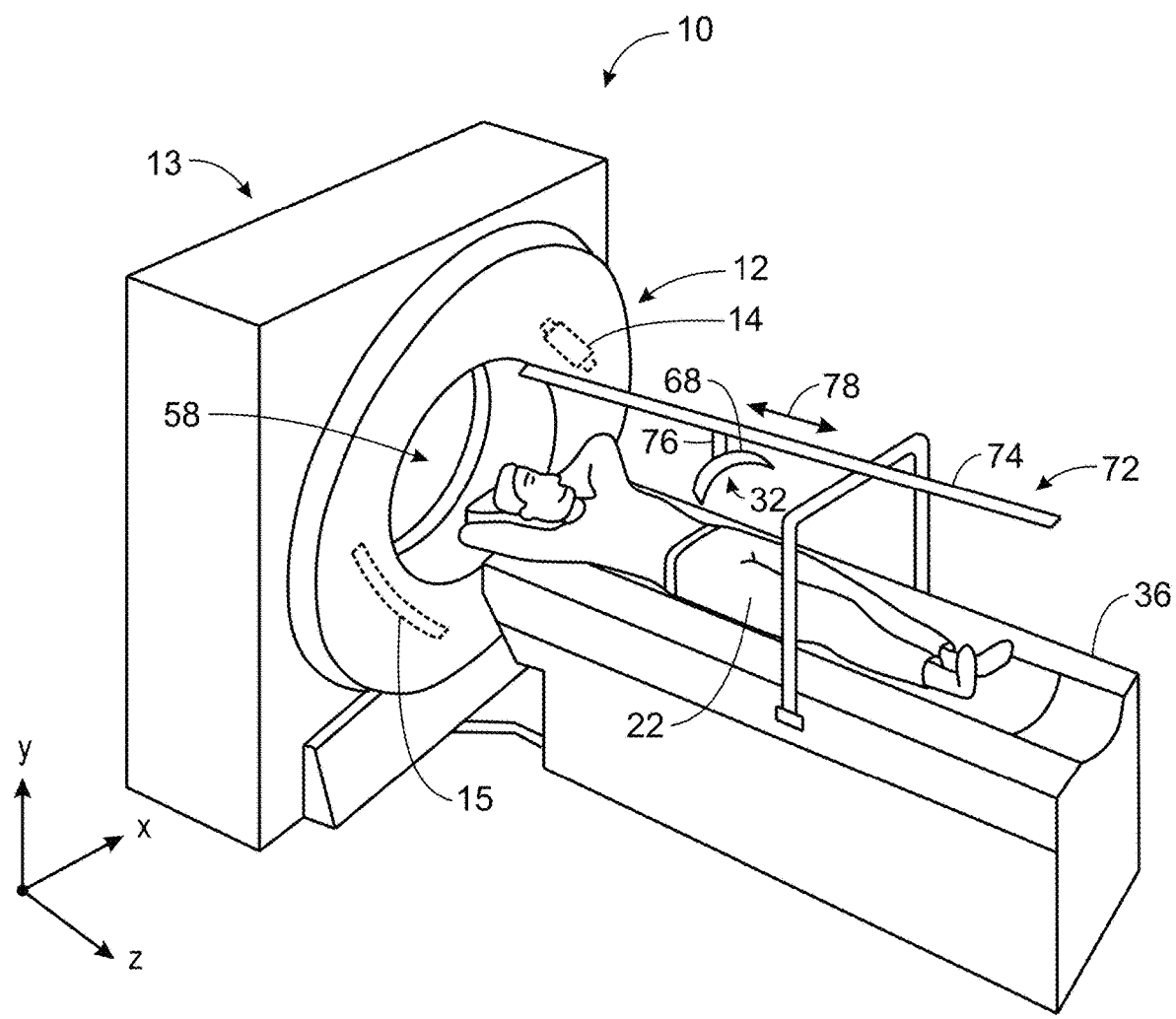
FIG. 10 is a pictorial representation of an external LiDAR scanning system coupled to a CT table, in accordance with aspects of the present disclosure.

In certain embodiments, the LiDAR scanning system 32 may be external to the gantry 12 but still physically coupled to the imaging system 10. FIG. 10 is a pictorial representation of an external LiDAR scanning system 32 coupled to the CT table 36. The LiDAR scanning system 32 is coupled to a guide rail system 72. The guide rail system 72 is coupled to the table 36. The guide rail system 72 is configured to move the LiDAR scanning system 32 toward and away from the gantry 12 (e.g., in the Z-direction along the longitudinal length of the patient 22). The guide rail system 72 includes a main guide rail 74 coupled to a support structure 76 that supports the main guide rail 74. The main guide rail 74 extends in the Z-direction above the table 36 (e.g., along a longitudinal length of the table 36). The support structure 76 is coupled to the table 36. The support structure 76 extends in a vertical direction (e.g., in the Y-direction) from the table 36 and then extends in a horizontal direction (e.g., in the X-direction) to couple to the main guide rail 74. The configuration of the support structure 76 and how it is coupled to both the table 36 and the main guide rail 74 may vary.

The LiDAR scanning system 32 includes the LiDAR panel 68 (e.g., having an arc shape). The LiDAR panel 68 includes a plurality of LiDAR scanners coupled to it. The plurality LiDAR scanners are circumferentially spaced apart along the arc of the LiDAR panel 68 at different angular positions to enable the acquisition of different views of LiDAR data. The LiDAR panel 68 is coupled to the guide rail system 72. In particular, the LiDAR panel 68 is coupled to the main guide rail 74 via a vertical support stanchion 76 (e.g., post or bar). The guide rail system 72 is configured to move the LiDAR panel 68 (and the vertical support stanchion) back and forth toward the gantry 12 as indicated by arrow 78 (in the Z-direction) along the main guide rail 74. The main guide rail 74 may include an actuation system (e.g., chain actuator, electro-mechanical linear actuator, or any other mechanism for facilitating linear movement along the main guide rail 74). In certain embodiments, the guide rail system 72 is configured to circumferentially move the LiDAR panel 68 along its arc. In particular, the guide rail system 72 may enable the LiDAR panel 68 to rotate circumferentially (e.g., relative to the axis of rotation 24 in FIG. 2) so that the LiDAR panel 68 is moving with respect to the vertical support stanchion 76. The LiDAR panel 68 may rotate both clockwise and counter-clockwise (e.g., relative to the axis of rotation 24 in FIG. 2). Rotational movement of the LiDAR panel 68 enables the acquisition of LiDAR data from additional different angular positions.

Figure 11A:
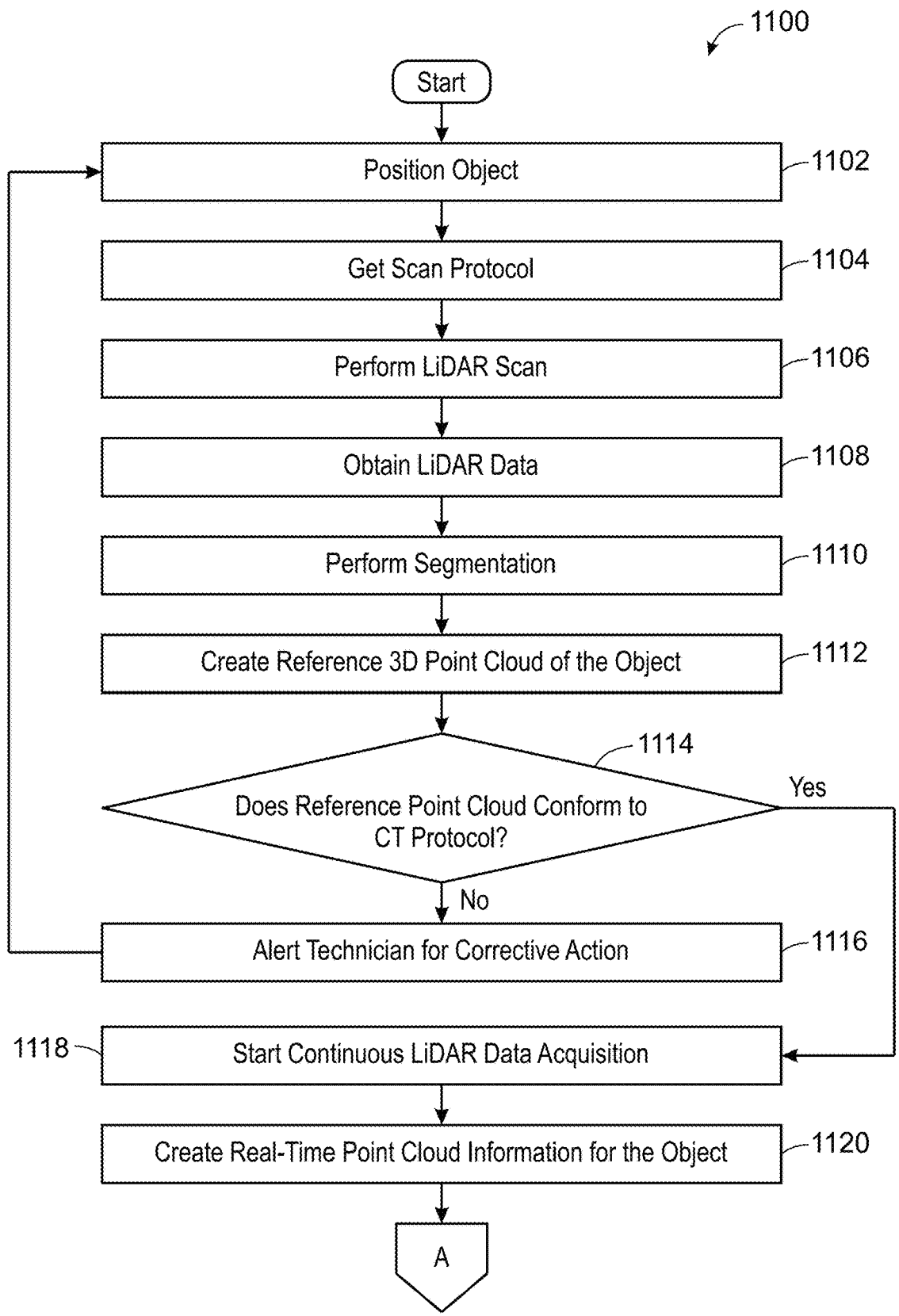
FIGS. 11A and 11B are a flowchart of a method for LiDAR guided auto gating in a CT imaging system.
Figure 11B:
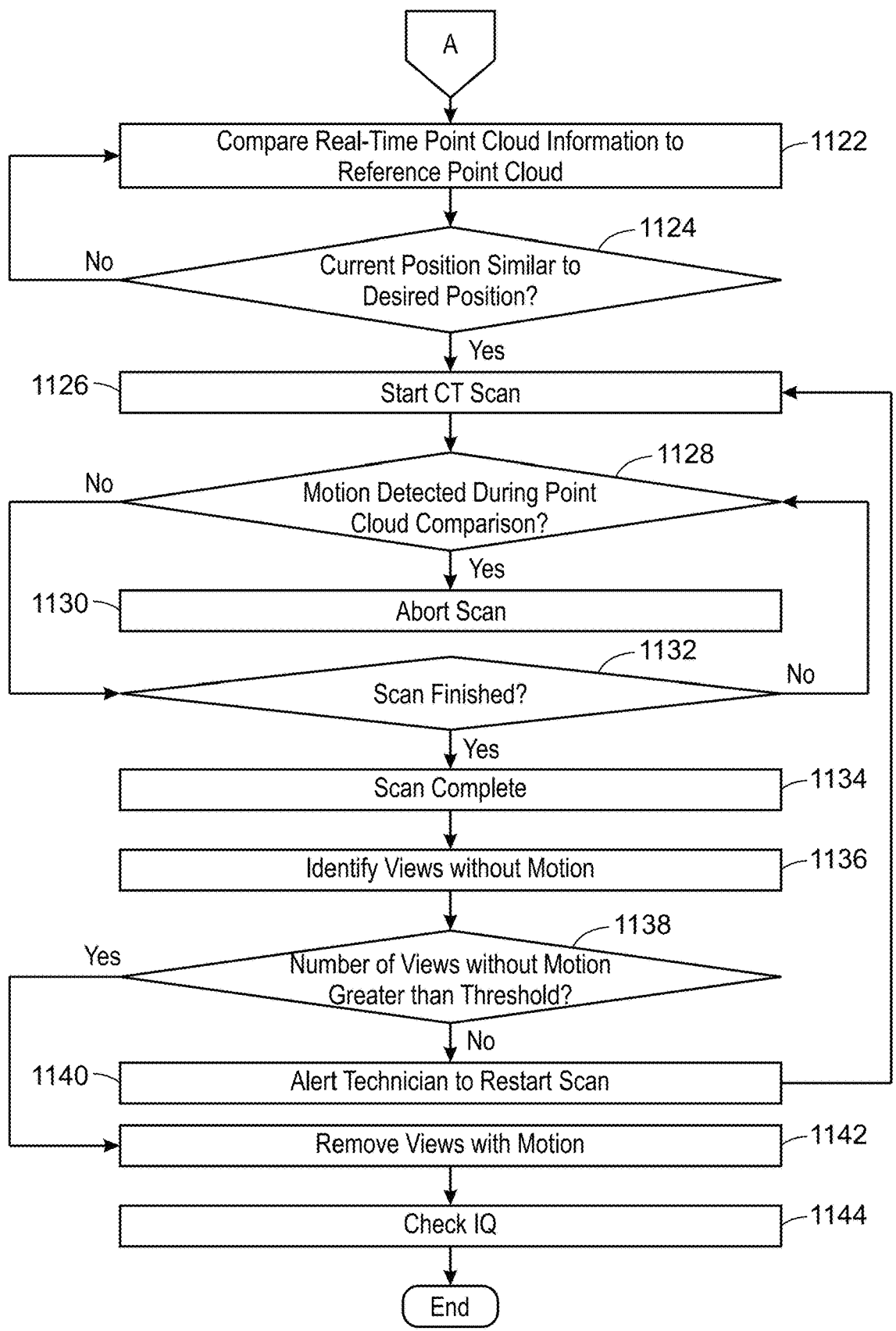

FIGS. 11A and 11B are a flowchart of a method for LiDAR guided auto gating in a CT scanner. The method begins at block 1102 with the object being positioned on the table 36 of the CT imaging system 10. In some examples, a user or technician positions an object on the table or assists a patient into position on the table. In other examples, a patient may position themselves on the table with assistance from the technician and/or imaging system. After the patient is positioned on the table, the CT imaging system obtains the scan protocol (block 1104). For example, the computer 42 associated with the CT imaging system obtains the scan protocol from mass storage 50, a remote server, and/or patient information. At block 1106, a LiDAR scan is performed on the patient, prior to initiation of a CT imaging scan. Baseline LiDAR data is obtained via the LiDAR scanning system (block 1108). Segmentation of the baseline LiDAR data is performed on the baseline LiDAR data using, for example, DBSCAN (block 1110). However, any other suitable segmentation technique may be used. The LiDAR data processing unit may perform the segmentation. Alternatively, the computer performs the segmentation. After the baseline LiDAR data is segmented, a reference or baseline 3D point cloud is created of the object (block 1112). The LiDAR data processing unit create the reference 3D point cloud. Alternatively, the computer creates the reference or baseline 3D point cloud information. The 3D point cloud may represent a topography of the patient undergoing the CT scan. Additionally, the 3D point cloud includes real-time positional information (patient motion information), which may be used to automatically trigger a CT acquisition when no patient motion is detected by the LiDAR system during a CT scan, and/or automatically abort a CT acquisition when patient motion is detected by the LiDAR system during a CT scan. The reference 3D point cloud may be used to determine the initial position of the object, which can be used to determine whether the object or portion of the object is correct for the given CT protocol, the position is correct for a given or selected CT protocol, whether the object has moved, etc.

In block 1114, it is determined (e.g., via the computer) the whether the reference point cloud conforms to the CT protocol. For example, the reference point cloud is analyzed to determine whether the correct portion of the object was scanned for the give CT protocol (e.g., a head of the patient scanned for a protocol requiring scan of the head of the patient, an abdomen of the patient scanned for a protocol requiring a chest scan, etc.). If the reference point cloud does not conform to the CT protocol, the technician is alerted to perform corrective action (e.g., via a message on the display or speaker of the imaging system) and the method returns to block 1102 to reposition the object. If the reference point cloud conforms to the CT protocol, the method continues. At block 1116, continuous LiDAR data acquisition is started. For example, during continuous LiDAR scanning, the LiDAR scanning system obtains LiDAR data continuously (e.g., the LiDAR scanning system initiates another scan immediately after completing a scan) (block 1118). Alternatively, the LiDAR scanning system may obtain LiDAR data at a set time interval (e.g., in milliseconds, in seconds, etc.). As the LiDAR scanning system obtains data from the continuous LiDAR data acquisition, real-time point cloud information for the object is created (block 1120). The real time-point cloud information may be used to determine, for example, whether the object moved and/or an amount of movement of the object. In block 1122, the real-time point cloud information is compared (e.g., using the computer) to the reference point cloud. In some examples, the baseline LiDAR data is compared to the continuously obtained LiDAR data. In some examples, as each point cloud is created from each scan during continuous LiDAR data acquisition, the new point cloud created is compared to the reference point cloud. In some examples, the real-time point cloud information is updated with changes to the acquired LiDAR data rather than creating a new point cloud, and as the point cloud is updated, the real-time point cloud is compared to the reference point cloud.

In block 1124, the computer, for example, determines whether the current position of the object is similar to the desired or initial position of the object based on the comparison of the reference point cloud and the real-time point cloud(s). If the current position is not similar to the desired position, the continuous LiDAR data acquisition and comparison of real-time point cloud information to reference point cloud information continues until the position is similar to the desired position. In some such examples, the technician may help reposition the object or patient using verbal signals or by physically repositioning the object or patient. If the current position is similar to the desired position, the CT imaging scan is initiated (block 1126). In some examples, the scan will be initiated if there is no motion of the patient detected. Some types of patient motion may include movement of the head (head motion), respiratory motion, or cardiac motion.

In some examples, initiating the CT imaging scan includes altering an operator (e.g., via a display) that the imaging scan can be initiated, and the operator initiates the scan. During the CT scan, LiDAR data collection continues (e.g., a LiDAR scan of the patient occurs during the CT scan) and real-time point cloud information is created and compared to reference point cloud information. To create real-time point cloud information, the LiDAR scan data may be processed during the continuous LiDAR data collection. At block 1128, it is determined (e.g., via the computer) if motion is detected during the point cloud comparisons. In some examples, detecting the motion also includes determining of the motion exceeds a threshold amount of motion. The threshold amount of motion may be a different amount for different scan protocols (e.g., may be defined by the scan protocol). If motion is detected, the scan is aborted (block 1130). If there is no motion detected, it will be determined whether the scan is finished (block 1132). If the scan is not finished, the method continues to determine if motion is detected throughout the duration of the CT scan. If the scan is finished, the scan is complete (block 1134). In some examples, an operator or technician receives a message via a display or speaker when the scan is complete.

In block 1136, the computer identifies views without motion. In some examples, the views without motion may includes views with motion under a predetermined threshold. This predetermined threshold for motion may be different (e.g., lower) than the threshold for motion that may be used when determining whether to abort the CT scan. The computer then determines if the number of views without motion is greater than a threshold number of views (block 1138). If the number of views without motion is not greater than the threshold number of views (e.g., a percentage of the total views), the technician is alerted via the display or speaker to restart the scan (block 1140). If the number of views without motion is greater than the threshold number of views, the views with motion are removed (block 1142). The image quality (IQ) of the CT scan results is then checked (block 1144). The method is complete.

While the example method is described as a whole, portions of the method may be used independently of the remainder of the method. For example, blocks 1102-1112, 1118-1122, and 1136-1144 may be used during a CT scan to determine which views have motion, and thus, should be removed from or if the scan should be restarted. In some examples, blocks 1102-1112 and 1118-1134 may be used to detect motion during a CT scan and abort the CT scan after detected motion. In some examples, blocks 1102-1116 may be used before a CT scan to confirm that the patient or object is in the correct position for the specific scan protocol before beginning an imaging scan. In other examples, other portions of the method 1100 may be excluded, or additional steps may be included and/or repeated. Although a CT system is described by way of example, it should be understood that the present techniques may also be useful when applied to images acquired using other imaging modalities, such as X-ray imaging systems, magnetic resonance (MR) imaging systems, positron emission tomography (PET) imaging systems, single-photon emission computed tomography (SPECT) imaging systems, ultrasound imaging systems, and combinations thereof (e.g., multi-modality imaging systems, such as PET/CT, PET/MR or SPECT/CT imaging systems). The present discussion of a CT imaging modality is provided merely as an example of one suitable imaging modality.

Figure 12:
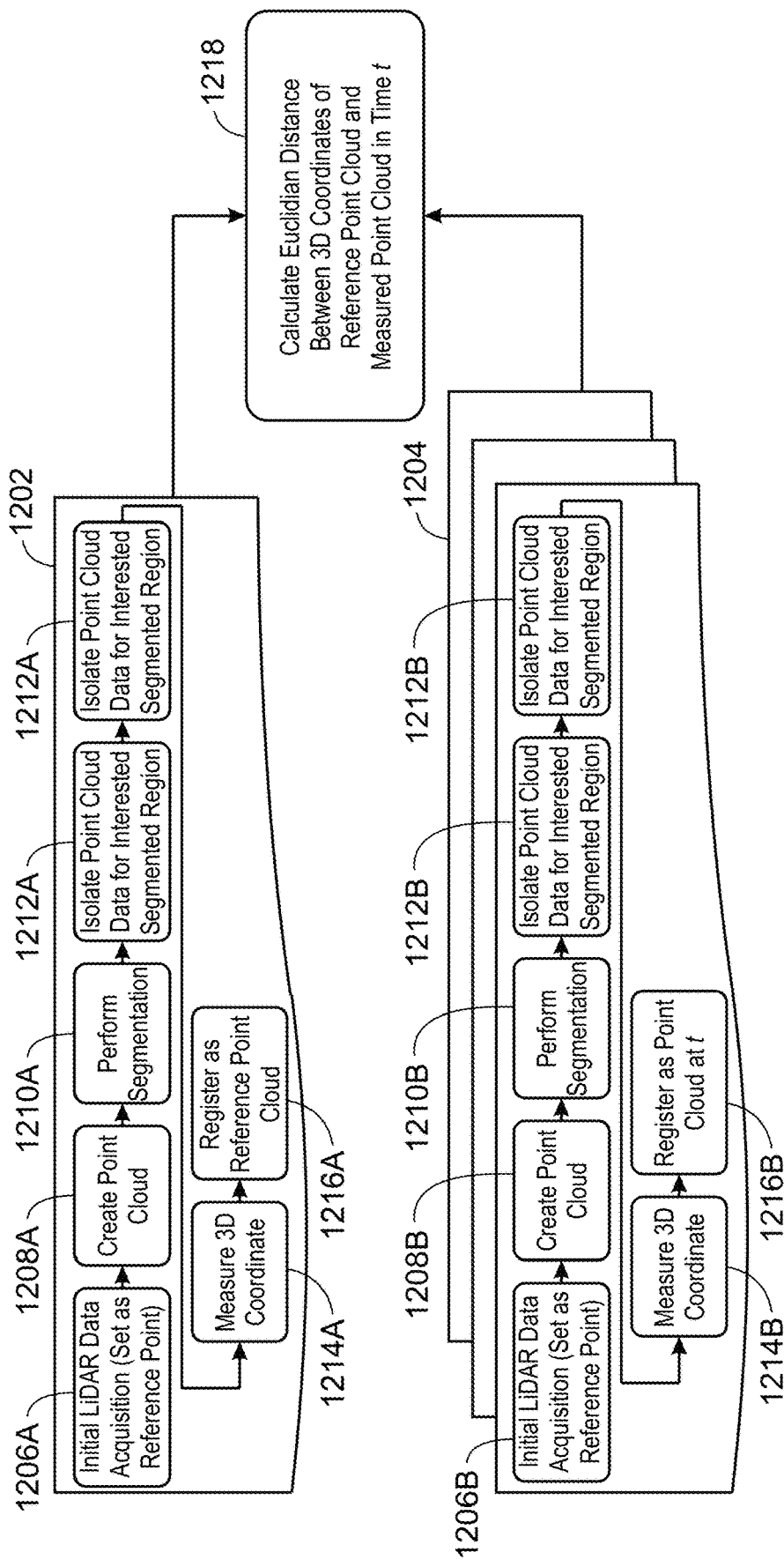
FIG. 12 is a pictorial representation of steps for data acquisition and motion detection.

FIG. 12 is a pictorial representation of steps for data acquisition and motion detection. Specifically, FIG. 12 is a detailed representation of LiDAR data acquisition, segmentation, creating 3D point clouds, and comparison of the point clouds. FIG. 12 depicts the steps of creating the initial or reference point cloud information in the single scan phase 1202 and the steps of creating a real-time point cloud information in the continuous scan phase 1204. Each phase 1202, 1204 begins with initial LiDAR data acquisition 1206A, 1206B. A point cloud is crated from the LiDAR data 1208A, 1208B, segmentation is performed 1210A, 1210B, and the point cloud data for interested segmented region is isolated 1212A, 1212B. 3D coordinates of each point in the point cloud are measured 1214A, 1214B and registered 1216A, 1216B as a point in the reference point cloud or in the real-time point cloud at a time t. Then, to compare the reference point cloud and the real-time point cloud, Euclidian distance is calculated between coordinates of reference points in the reference point cloud and each point cloud at various times t 1218. This process may be used in tandem with the method 1100 described in conjunction with FIGS. 11A and 11B.

Figure 14C:
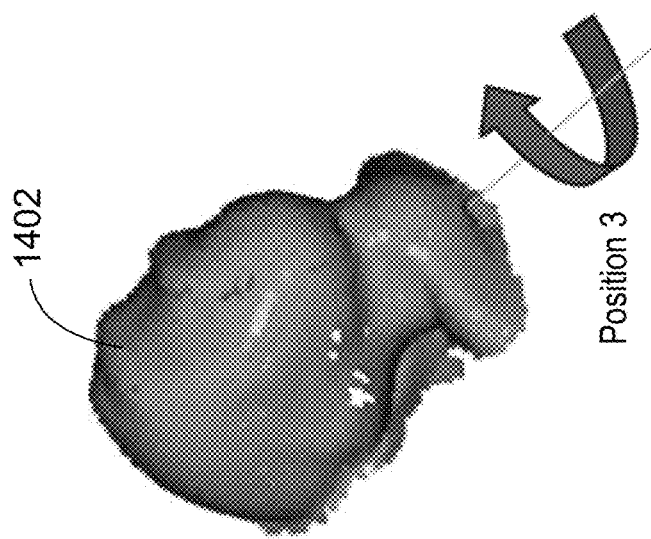
FIGS. 14A-14C depict head movement during data acquisition using a CT imaging system.
Figure 14B:
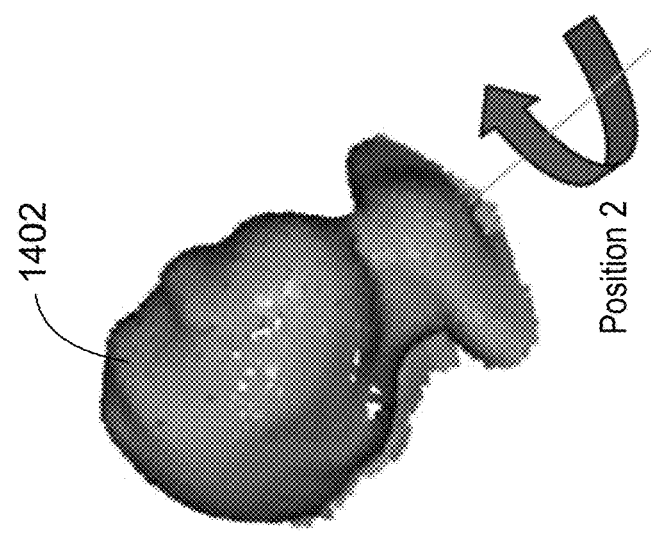
Figure 14A:
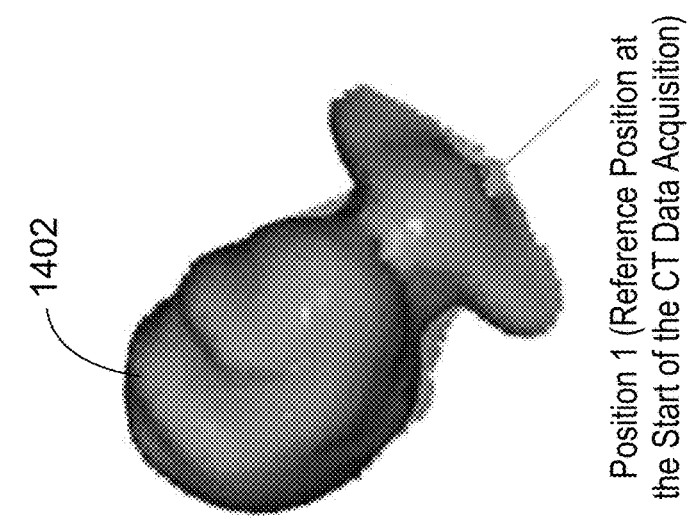

FIG. 13A is an image depicting LiDAR data of an example phantom head 1302. FIG. 13B is an image depicting the segmentation of the example phantom head 1302 of FIG. 13A from the same perspective. FIGS. 14A-14C are images that depict head movement during data acquisition using a CT imaging system. FIG. 14A depicts a head 1402 in an initial position. FIGS. 14B and 14C depict the example head 1402 progressively rotating clockwise. In some examples, the amount of movement between images in FIGS. 14A and 14B and/or 14C is enough to prevent initiation of the imaging scan or to abort imaging acquisition. Alternatively, the views acquired during the movement may be removed after the scan due to detected movement.

FIG. 15 depicts an example 3D segmented LiDAR point cloud 1502 created using data obtained using the LiDAR scanning system. Each point 1504 in the example point cloud 1502 of FIG. 15 may be registered (e.g., the coordinates of each point are registered) and then compared with corresponding points in other point clouds. In some examples, a pre-determined number of points 1504 is used to create a point cloud 1502 for a region. Alternatively, the number of points 1504 is determined based on the size and/or shape of the region or object.

FIGS. 16A and 16B depict examples of motion artifacts in images obtained during a CT scan. The motion artifacts negatively impact image quality. The example systems and method discussed herein to detect motion of an object may be used to improve image quality by reducing the number of views obtained when the object is in motion, or by aborting the scan if the object moves during the scan.

FIGS. 17A and 17B depict example detailed representations of LiDAR data and segmented LiDAR data. FIG. 17A is an image depicting LiDAR data of an example phantom head 1702 and torso 1704. FIG. 17B is an image depicting the segmentation of the example phantom head 1702 and torso 1704 of FIG. 17A from the same perspective.

FIGS. 18A-18C depict example segmented LiDAR point clouds 1802 and 1806 of regions isolated from the LiDAR scanning data. In particular, FIG. 18A depicts a point cloud for a torso 1804 of a subject. A segment of the torso 1808 may be selected as the region of interest 1806. FIGS. 18B and 18C are depictions of the isolated region of interest 1806 from the torso 1804. The LiDAR scanning system may only alert the operator of movement in the region of interest 1806, and not about movement in areas outside of the region of interest 1804. Thus, the images taken of the region of interest have an improved image quality, as discussed in conjunction with the method described in FIGS. 11A and 11B. Meanwhile, movement in other regions (e.g., upper torso, head) will not affect the image acquisition.

Technical effects of the disclosed embodiments include providing systems and methods for generating an accurate 3D measurement of a target (e.g., patient) before or during a CT scan to be utilized in a subsequent CT workflow process for the CT scan. The present disclosure provides systems and methods for incorporating LiDAR based techniques with a CT imaging system to aid various workflows more efficiently. The disclosed embodiments provide a method for detecting the movement of a subject during an imaging scan and adjust the scan based on the detected movement by aborting the scan or removing imaging views that include movement, thereby increasing the image quality.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A method of creating representative position information of a patient during a medical imaging scan, the method comprising:
 prior to performing the medical imaging scan, performing an initial LiDAR data acquisition to obtain baseline LiDAR data;
 performing segmentation of the baseline LiDAR data, wherein the baseline LiDAR data includes a three-dimensional (3D) point cloud model;
 performing continuous LiDAR data acquisition to obtain continuous LiDAR data, which includes a real-time 3D point cloud model; and
 comparing the continuous LiDAR data with the baseline LiDAR data to detect motion of the patient.

2. The method of claim 1, further comprising determining if the baseline LiDAR data conforms to a selected CT protocol.

3. The method of claim 2, further comprising alerting an operator that the baseline LiDAR data conforms to the selected CT protocol prompting the operator to initiate the medical imaging scan.

4. The method of claim 2, further comprising prompting an operator to perform a corrective action if the baseline LiDAR data does not conform to the selected CT protocol.

5. The method of claim 3, further comprising aborting the medical imaging scan if the motion of the patient exceeds a threshold during the medical imaging scan.

6. The method of claim 1, further comprising prompting an operator to initiate the medical imaging scan.

7. The method of claim 1, further comprising identifying views of the medical imaging scan without motion of the patient detected.

8. The method of claim 7, further comprising transferring the views without motion to a reconstruction algorithm to be used in reconstruction.

9. The method of claim 6, further comprising determine if a number of views is greater than a threshold.

10. The method of claim 7, wherein if a number of views is greater than a threshold, prompting an operator to initiate a re-scan of the patient.

11. A medical imaging system, comprising:
 a computed tomography (CT) imaging system, comprising:
  a gantry having a bore, rotatable about an axis of rotation;
  an X-ray source mounted on the gantry and configured to emit an X-ray beam;
  an X-ray controller to operate the X-ray source; and
  an X-ray detector configured to detect the X-ray beam emitted by the X-ray source;
 a laser imaging, detection and ranging (LiDAR) scanning system coupled to the CT imaging system, wherein the LiDAR scanning system includes:
  a LiDAR instrument mounted on the gantry;
  a LiDAR controller to control operation of the LiDAR instrument; and
  a LiDAR data processing unit to obtain pre-scan data from the LiDAR instrument, wherein the LiDAR data processing unit generates a baseline 3D point cloud information of a subject using the pre-scan data, and wherein the LiDAR data processing unit obtains real-time data during an imaging scan to generate additional 3D point cloud information, wherein the real-time data is compared to the pre-scan data to detect movement of the subject; and a processor to, when the LiDAR data processing unit detects movement of the subject, abort the imaging scan.

12. The system of claim 11, further comprising determining if the pre-scan data conforms to a selected CT protocol.

13. The system of claim 12, wherein the processor is to alert an operator to initiate the imaging scan if the pre-scan data to the selected CT protocol.

14. The system of claim 12, further comprising a display, wherein a prompt is provided to an operator via the display to perform a corrective action if the pre-scan data does not conform to the selected CT protocol.

15. The system of claim 11, wherein the processor is to identify views of the imaging scan without motion of the subject detected.

16. The system of claim 15, wherein the processor is to further transfer the views without motion to a reconstruction algorithm to be used in reconstruction.

17. The system of claim 16, wherein the processor is to determine if a number of views is greater than a threshold.

18. The system of claim 17, wherein if the number of views is greater than the threshold, the processor is to prompt an operator to initiate a re-scan of the subject.

* * * * *